United States Patent
Berg

(10) Patent No.: US 7,126,011 B2
(45) Date of Patent: Oct. 24, 2006

(54) PROCESS FOR THE PREPARATION OF THIOXANTHONES

(75) Inventor: Carsten Berg, Borre (DK)

(73) Assignee: Prom Limited (GB)

( * ) Notice: Subject to any disclaimer, the term of this patent is extended or adjusted under 35 U.S.C. 154(b) by 172 days.

(21) Appl. No.: 10/408,332

(22) Filed: Apr. 7, 2003

(65) Prior Publication Data
US 2003/0229233 A1 Dec. 11, 2003

Related U.S. Application Data

(63) Continuation-in-part of application No. PCT/GB00/04343, filed on Nov. 15, 2000.

(60) Provisional application No. 60/375,435, filed on Apr. 26, 2002.

(51) Int. Cl.
*C07D 335/08* (2006.01)
(52) U.S. Cl. .................................................. 549/27
(58) Field of Classification Search ................ 549/27
See application file for complete search history.

(56) References Cited

U.S. PATENT DOCUMENTS

| | | | | |
|---|---|---|---|---|
| 4,101,558 | A | | 7/1978 | Vacek et al. ................ 260/328 |
| 4,505,794 | A | * | 3/1985 | Kvita et al. ................. 522/14 |
| 4,506,083 | A | * | 3/1985 | Kvita et al. ................. 549/27 |
| 5,380,749 | A | * | 1/1995 | Miller et al. ................ 514/437 |
| 5,916,984 | A | * | 6/1999 | Bearson et al. ............. 526/204 |
| 6,025,408 | A | * | 2/2000 | Williams et al. ............ 522/53 |

FOREIGN PATENT DOCUMENTS

GB  2 050 378  1/1981

OTHER PUBLICATIONS

Bernard Belleau et al., Synthetic Communications, (1983), 13(12), 977-984; "O-Chlorosulfenylbenzoyl Chloride: A Useful Reagent in the Synthesis of Thioxanthones".

Smiles, J. Chem. Soc. (1911), 99, 640-649; "LXXII.-The Interaction of Aromatic Disulphides and Sulphuric Acid".

Copy of the International Search Report dated Aug. 20, 2001.

* cited by examiner

*Primary Examiner*—Deborah C. Lambkin
(74) *Attorney, Agent, or Firm*—Nields & Lemack

(57) ABSTRACT

Processes are described for the preparation of thioxanthones (Formula I). A reactant mixture of a 2-chlorothiobenzoyl chloride (Formula II) and an aromatic compound (Formula III) is added to a slurry of a Friedel-Crafts catalyst in an organic Friedel-Crafts solvent. Products of the processes may be used for the preparation of a pharmaceutical product for use in the field of psycho-therapeutics, or as activators or sensitizers in the photo-polymerization of ethylenically unsaturated monomers Formula I
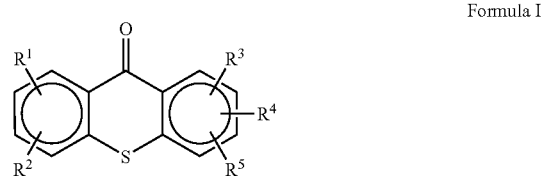

Formula II
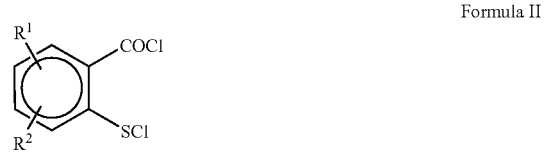

Formula III

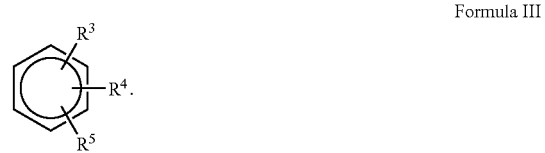

13 Claims, No Drawings

PROCESS FOR THE PREPARATION OF THIOXANTHONES

This application is a continuation-in-part of International Application PCT/GB00/04343, with an international filing date of Nov. 15, 2000, published in English under PCT Article 21(2) and also claims priority of Provisional Application Ser. No. 60/375,435 filed on Apr. 26, 2002, the disclosures of which are hereby incorporated by reference.

FIELD OF THE INVENTION

The present invention relates to a process for preparing thioxanthones of Formula I:

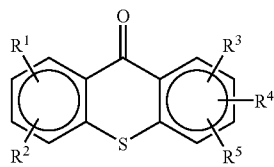

Formula I the products of such a process and the use of such products.

BACKGROUND OF THE INVENTION

Thioxanthones are useful intermediates for the preparation of pharmaceuticals in the field of psychotherapeutics and are used as activators or sensitizers in the photopolymerisation of ethylenically unsaturated monomers.

Basically thioxanthones are formed by cyclisation of 2-phenylthiobenzoic acid derivatives. As described by Smiles, J. Chem. Soc. (1911), 99, 645, this reaction can be performed in one step, by reacting 2,2'-dithiodibenzoic acid with an aromatic compound in sulfuric acid. The main drawbacks of the process are that yields are poor at 40–60%, a large excess of sulfuric acid has to be used, after reaction a large amount of dilute sulfuric acid has to be regenerated or disposed of and sulfonated aromatics are major by-products.

For these reasons, 2-chlorothiobenzoyl chloride (CTBC) or derivatives thereof have been considered as an obvious choice for a Friedel-Crafts type reaction to form thioxanthones. This reaction is first disclosed in U.S. Pat. No. 4,101,558, where 2-chlorosulfenylbenzoyl- or 5-chloro-2-chlorosulfenylbenzoyl chloride are reacted with benzene, chlorobenzene or biphenyl to form thioxanthone, 4,7-chlorothioxanthone and 2,7-dichlorothioxanthone, 2- and 4-chlorothioxanthone and 7-chloro-2-phenylthioxanthone in the presence of aluminum chloride as catalyst. The 2-chlorosulfenylbenzoyl chloride and the aromatic substrate are mixed in a suitable solvent and aluminum chloride is added in portions, giving rise to product yields from 70–91%. Applicants performed experiments under the conditions disclosed in U.S. Pat. No. 4,101,558. CTBC and isopropyl benzene (cumene) in 1,2-dichloroethane (DCE) were reacted in the presence of aluminum chloride. The isomer content of isopropyl thioxanthone in the organic phase was found to be 70% of theory and 50% as isolated yield.

Bernard Belleau et al., Synth. Commun., (1983), 13, 977–984, have investigated different types of Lewis acids as catalyst to form thioxanthones from CTBC and benzene, ortho-/para-xylene or 1,4-dimethoxy substituted benzene. Tin(IV)chloride was found to be the most effective catalyst.

The experimental section describes mixing CTBC in a chlorinated solvent with tin(IV) chloride, after which the substrate is added in one lot. An attempt to perform the Friedel-Crafts reaction under the conditions described by Bernard Belleau et al. failed as CTBC disproportionated with aluminum chloride in DCE.

SUMMARY OF THE INVENTION

Surprisingly, it was found that thioxanthones could be obtained in high yield, purity and/or selectivity if a mixture of a 2-chlorothiobenzoyl chloride and an aromatic compound is added to a slurry of a Friedel-Crafts catalyst.

Consequently, the present application relates to a process for the preparation of a thioxanthone of Formula I:

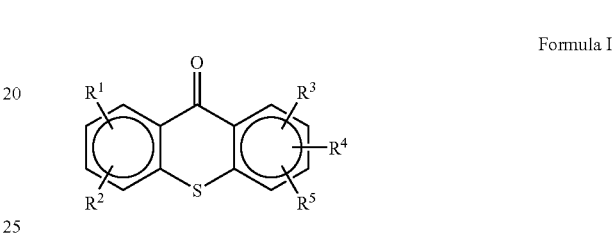

Formula I characterized in that a mixture of a 2-chlorothiobenzoyl chloride of Formula II:

Formula II or a mixture of 2-chlorothiobenzoyl chlorides of Formula II and an aromatic compound of Formula III:

Formula III is added to a slurry of an effective amount of a Friedel-Crafts catalyst, wherein the molar proportion of Formula II and III is from 1:1 to 1:20, $R^1$ and $R^2$ are independently from each other hydrogen, halogen, $C_{1-10}$-alkyl, $C_{6-12}$-aryl or $C_{1-10}$-alkoxy radicals, $R^3$, $R^4$ and $R^5$ are independently from each other hydrogen, halogen, hydroxyl, $C_{1-10}$-alkyl, $C_{5-8}$-cycloalkyl, $C_{6-12}$-aryl, $C_{1-10}$-alkoxy, —$X^1$—C(O)O$R^6$ —C(O)$R^7$—C(O)O$R^8$ or —C(O)N$R^9R^{10}$, wherein $X^1$ is $C_{1-10}$-alkylene, $R^6$, $R^7$ and $R^8$ are independently from each other $C_{1-10}$-alkyl, $C_{6-12}$-aryl or $C_{7-11}$-aralkyl and $R^9$ and $R^{10}$ are independently from each other hydrogen, $C_{1-10}$-alkyl, $C_{6-12}$-aryl or $C_{7-11}$-aralkyl, or $R^3$ and $R^4$ form a 5-, 6- or 7-member ring fused to the aromatic ring.

The process of the present invention can provide thioxanthones of the Formula I in high yield, purity and/or selectivity. For example, after water quench the total yield of isopropyl thioxanthone (ITX) isomers in the organic phase is about 93% of theory containing 13.2% 4-isopropyl-, 81.4% 2-isopropyl- and 3.3% x-isopropyl thioxanthone. Recrystallisation in methanol yields 12.6 g ITX (yield: 76% of theory; purity: 99.8% (HPLC) as white crystals, containing 11.2% 4-isopropyl-, 86.5% 2-isopropyl and 1.4% x-isopropyl thioxanthone (1-isopropyl- and/or 3isopropylthioxantone).

In Formulae I, II and III the substituents have the following meanings:

$C_{1-10}$-alkyl is typically linear or branched—where possible—methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, preferably C1–4-alkyl such as methyl, ethyl, n-propyl, isopropyl, n-butyl, sec.-butyl, isobutyl, tert.-butyl.

Examples of $C_{1-10}$-alkoxy are methoxy, ethoxy, n-propoxy, isopropxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably C1–4-alkoxy such as methoxy, ethoxy, n-propoxy, isopropoxy, n-butoxy, sec.-butoxy, isobutoxy, tert.-butoxy.

The term "$C_{6-12}$-aryl group" is typically phenyl, 1-naphthyl or 2-naphthyl, which may be unsubstituted or substituted.

The term "$C_{7-11}$-aralkyl group" is typically benzyl, 2-benzyl-2-propyl, β-phenyl-ethyl or α,α-dimethylbenzyl.

The term "$C_{5-8}$-cycloalkyl group" is typically cyclopentyl, cyclohexyl or cycloheptyl, which may be unsubstituted or substituted.

The above-mentioned substituents can be substituted by a $C_{1-10}$-alkyl, a hydroxyl group, a mercapto group, $C_1$–$C_8$-alkoxy, halogen a cyano group or an amino group.

Halogen means fluoride, chlorine, bromine and iodine, preferably chlorine.

$R^1$ and $R^2$ are preferably hydrogen, chlorine, bromine, phenyl, $C_{1-4}$-alkyl, in particular methyl, ethyl and isopropyl, or $C_{1-4}$-alkoxy, in particular methoxy and propoxy radicals.

$R^3$, $R^4$ and $R^5$ are preferably hydrogen, chlorine, bromine, hydroxyl, $C_{1-4}$-alkyl, or $C_{1-4}$-alkoxy. If $R^3$ and $R^4$ form a ring, it is preferably a phenyl ring. If $R^3$, $R^4$ and $R^5$ are groups of the formula —$X^1$—C(O)O$R^6$, —C(O)$R^7$, —C(O)O$R^8$, or —C(O)N$R^9R^{10}$, $X^1$ is preferab;y $C_{1-4}$-alkylene, in particular methylene and ethylene, $R^6$, $R^7$ and $R^8$ are preferably $C_{1-4}$-alkyl, in particular methyl or ethyl, and $R^9$ and $R^{10}$ are preferably hydrogen or $C_{1-4}$-alkyl.

The thioxanthone of the Formula I is preferably a 1-chloro-4-propoxythio, 2-chloro-, 4-chloro-, 2-bromo-, 4-bromo-, 2,4-diethyl-, 2,7-dichloro-, 2-hydroxy, 2-methyl-, 4-methyl-, 2-isopropyl-, 4-isopropyl- or 2-ethoxycarbonyl-methyl thioxanthone including mixtures of said thioxanthones with isomers which are obtained when carrying out the process of the present invention. Especially preferred are 1-chloro-4-propoxythioxanthone, 2- and 4-isopropylthioxanthone or a mixture of 2- and 4-isopropylthioxanthone, 2,4-diethylthioxanthone and a mixture of mainly 2,4-diethylthioxanthone and other diethyl isomers as well as 2- and 4-chlorothioxanthone or a mixture of 2- and 4-chlorothioxanthone.

As the aromatic compound of Formula III can also act as solvent, the molar proportion of Formula II and III is generally from 1:0.8 to 1:20. It is, however, preferred that the molar proportion of Formula II and III is from 1:1 to 1:1.2.

The Friedel-Crafts catalyst is generally used in an amount of 1.0 to 5 moles, preferably with a small molar excess of catalyst per mol of the 2-chlorothiobenzoyl chloride of Formula II. The preferred molar ratio is between 1.0:1 and 2.5:1, especially between 1.0:1 and 1.6:1.

Accordingly, the reaction is preferably carried out using the compound of Formula II, the aromatic substrate of Formula III and the Friedel-Crafts catalyst in a molar ratio of 1:0.8:1 to 1:20:5. A small molar excess of the aromatic substance is preferred. We have found that molar ratio of the components of 1:1.0:1.2, or 1:1.2:1.6 are particularly advantageous.

Suitable Friedel-Crafts catalysts are $BF_3$, $BCl_3$, $BBr_3$, $BeCl_2$, $ZnCl_2$, $GaCl_3$, $GaBr_3$, $BiCl_3$, $SbCl_3$, $TiCl_4$, $ZrCl_4$ and $SbCl_5$. Preferred Friedel-Crafts catalysts are aluminum chloride, aluminum bromide, tin(II) chloride, tin(IV) chloride and iron(III) chloride, wherein aluminum chloride and iron (III) chloride are especially preferred. The choice of the Friedel-Crafts catalyst can influence the selectivity. The use of iron(III) chloride at a reaction temperature of 20° C. produced less 1- and 3-isopropyl isomers in comparison to the use of aluminum chloride under the same conditions.

The process is carried out in organic solvent which are known to be useful for Friedel-Crafts reactions such as methylene chloride, 1,2-dichloroethane, 1,1,2,2-tetrachloroethane, dichlorobenzene, carbon disulfide or nitrobenzene, wherein 1,2-dichloroethane is especially preferred as solvent. Moreover, as already pointed out above the organic solvent may include the reactant of Formula II such as benzene, chlorobenzene, ortho-dichlorobenzene, bromobenzene, ortho-dibromobenzene, the alkylated benzenes such as toluene or isopropyl benzene, alkyl phenols such as 4-methylphenol or 2-tert-butyl-4-methylphenol, or phenyl ethers such as anisole.

The reactants represented by Formulas II and III are usually dissolved in 1 to 300, in particular 1 to 30 parts by weight of the organic solvent.

The slurry is usually formed between the Friedel-Crafts catalyst and 1 to 200, in particular 1 to 20 parts by weight of the organic solvent.

The reaction temperature during the addition of the reactants of the Formula II and III is maintained in the range of −10 to 50° C., in particular in the range of −10 to 30° C. The reactants of the Formula II and III are slowly added to the slurry of the Friedel-Crafts catalyst over a period of 20 minutes to 2 hours and following the addition, the obtained mixture may be stirred for 20 minutes to 2 hours at a temperature of 0 to 80° C., in particular 20 to 50° C. In case of isopropyl thioxanthone GC and GC-MS analysis has revealed that the distribution of different isomers can depend on the reaction temperature favoring 2- and 4-isopropyl isomers at lower temperatures and giving rise to a higher content of x-isopropyl isomers at elevated temperatures.

The starting materials of Formula II and III are known compounds or can be prepared in analogy to known procedures. 2-chlorothiobenzoyl chloride or substituted derivatives thereof are, for example, prepared by transforming 2,2'-dithiodibenzoic acid or substituted derivatives thereof to the acid chloride by reaction with thionyl chloride or a similar reagent. The reaction is facilitated by using thionyl chloride as solvent and by the addition of a catalyst of the amide type like dimethylformamide or N-methyl-2-pyrrolidinone. The acid chloride is chlorinated with chlorine or sulfuryl chloride revealing 2-chlorothiobenzoyl chloride or substituted derivatives thereof. It can be advantageous to distill the starting material of the Formula II before it is used in the Friedel-Crafts reaction. Brown crude CBTC can, for example, be purified by a vacuum distillation at 80 to 200° C. and a pressure of 0.1 to 300 mm Hg, preferably at 165–170° C. and a pressure of 10 mm Hg, giving a light yellow product with m.p. 67–68° C. As CTBC was found to be heat sensitive by prolonged heating to about 200° C., the distillation should preferably be performed under mild conditions like falling- or wiped-film evaporations to avoid decomposition at industrial scale.

The method of isolating the product from the reaction mixture may vary depending on the physical and chemical character of the thioxanthone of Formula I and on the degree of purity required of the product. If the complex between the product and aluminum chloride is sparingly soluble, it can be an advantage to isolate the complex before decomposition. Decomposition of the complex can be accomplished with water, with diluted mineral acid or with aqueous solutions of alkaline hydroxides, e.g. sodium, potassium, barium or calcium hydroxide. The choice of decomposition medium depends on the nature of the product and its insoluble by-products keeping the product in the organic phase and the by-products int he water phase. Crude thioxanthones are isolated by evaporation of the solvent and if necessary purified by methods such as distillation, crystallization, chromatography, etc.

The products of the processes according to the invention may be used for the preparation of a pharmaceutical product for use in the field of psycho-therapeutics, or as activators or sensitizers in the photo-polymerization of ethylenically unsaturated monomers.

The following examples are for purposed of illustration and are not intended to limit the scope of the present invention in any manner whatsoever. Parts and percentages are by weight unless otherwise specified.

EXAMPLES

Reaction mixtures and products were analyzed by HPLC, GC and GC-MS. Specific compounds were characterized by comparison with authentic samples.

HPLC Conditions:
Column: Merck, LiChrospher 100-RP 18, 5 micron 250×4 mm;
Detector wavelength: 230 nm;
Injection volume: 20 μl;
Flow rate: 2 ml/min;
Eluents: A: 0.005 M $H_3PO_4$ in water; B: acetonitrile;
Gradient: Time 0, % B 40; 10, 90; 15, 90; 20, 40;
Isocratic: % B 66.

GC Conditions:
Column: Restek, MTX-5; 30 m; 0.53 mm/D; 1.0 μm df.
Carrier gas: Nitrogen, psi
Detector: FID
Temperature: 230° C., isocratic Example 1

2-Chlorothiobenzoyl Chloride (CTBC)

100 g 2,2"-dithiodibenzoic acid (assay 95%) and 1.0 g 1-methyl-2-pyrrolidone are added to 260 g thionyl chloride. The stirred slurry is heated slowly to reflux at 80° C., until a clear solution has been achieved and HCl evolution has been ceased. The mixture was cooled to 50° C. and 48.6 g sulfuryl chloride are slowly introduced. Stirring is continued for 30 min, after which volatiles were evaporated on a rotary evaporator leaving 140.0 g crude CTBC as a light brown solid. The product is vacuum distilled through a short Vigreux column at 165–170° C., 10 mm Hg, affording 119.5 g CTBC (yield: 93% of theory; purity: 98.5%) as a light yellow crystalline product. The purity is estimated by derivatization of CTBC with ammonia to 1,2-benzisothiazolin-3-one and analyzing the solution by HPLC.

Example 2

2-/4-Isopropylthioxanthone (ITX)

40.6 g crude CTBC (95% assay) and 23.6 g cumene are dissolved in 200 g 1,2-dichloroethane. This solution is added over a period of 45 min to a stirred slurry of 32.7 g aluminum chloride in 200 g DCE, covered with nitrogen, at a temperature of 15 to 20° C. The mixture is stirred at 25° C. for 30 min, after which the reaction mixture is poured into 500 ml water with vigorous stirring. The organic phase is separated and washed with 200 ml water and water/50% sodium hydroxide to pH 12, evaporated in vacuum leaving 45 g of an oil, which was distilled at 225° C., 5 mm Hg, giving 36.9 g of a fraction (yield: 78% of theory) consisting according to GC analysis of 12% 4-Isopropyl-, 76% 2-isopropyl- and 12% x-isopropyl thioxanthone.

Example 3

ITX 13.4 g distilled CTBC and 7.8 g cumene are mixed in 56 g DCE. The solution was added to a stirred slurry of 10.8 g aluminum chloride in 100 g DCE at a temperature of −10 to −5° C. within a period of 30 min. The mixture is stirred for further 30 min, allowed to warm to 10° C. and then poured into 200 ml water. The organic phase is separated, washed with water and sodium hydroxide to pH 14 and evaporated in vacuum, leaving 14.8 g of crude ITX as an oil, consisting (according to HPLC analysis) of 93% ITX isomers consisting (according to GC analysis) of 13.2% 4-isopropyl-, 81.4% 2-isopropyl- and 4.1% x-isopropyl thioxanthone. Recrystallisation in methanol yields 12.6 g ITX (yield: 76% of theory; purity: 99.8% (HPLC) as white crystals, containing 11.2% 4-isopropyl-, 86.5% 2-isopropyl and 1.4% x-isopropyl thioxanthone.

Example 4

ITX 8.6 g of distilled CTBC and 5.0 g cumene are dissolved in 60 g DCE and added to a stirred slurry of iron(III) chloride in 100 g DCE over 30 min at a temperature of 20° C. The reaction mixture is poured slowly into 200 ml dilute hydrochloric acid and washed with 100 ml water and evaporated in vacuum, leaving 9.8 g crude ITX as an oil, consisting (according to HPLC analysis) of 80.9% ITX isomers consisting (according to GC analysis) of 10.8% 4-isopropyl-; 81.3% 2-isopropyl- and 3.7% x-isopropyl thioxanthone. Recrystallisation in methanol yields 8.0 g ITX (yield: 76% of theory; purity: 95.6% (HPLC( ) as light yellow crystals, containing 9.8% 4-isopropyl-, 88.2% 2-isopropyl and 1.0% x-isopropyl thioxanthone.

Example 5

2-/4-Chlorothioxanthone (CTX)

10.5 g crude CTBC (95% assay) and 6.7 g chlorobenzene dissolved in 16 g DCE are added over 30 min to a stirred slurry of aluminum chloride in 150 g DCE, covered with nitrogen, at a temperature of 40–45° C. The reaction mixture is stirred for further 30 min at 40° C. and poured into stirred water keeping pH at 12 by adding 50% sodium hydroxide. The DCE phase is separated and washed once with water. A HPLC run revealed a content of 11.1 g of CTX (yield: 94% of theory). The solvent is evaporated in a rotary evaporator under vacuum to a weight of 20.1 g. Crystals are isolated, washed with ethanol and dried, affording 8.6 g CTX (yield: 73% of theory; purity: 98.8% (HPLC), m.p. 143–145° C.).

What is claimed is:

1. A process for the preparation of at least one thioxanthone represented by Formula I:

Formula I

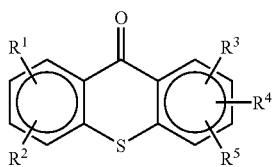

which process comprises adding a reactant mixture of a 2-chlorothiobenzoyl chloride represented by Formula II:

Formula II

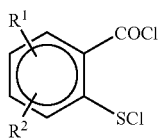

and an aromatic compound represented by Formula III:

Formula III

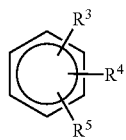

to a slurry of a Friedel-Crafts catalyst in an organic Friedel-Crafts solvent, wherein:

$R^1$ and $R^2$ are each independently selected from hydrogen, halogen, $C_{1-10}$-alkyl, $C_{6-12}$-aryl or $C_{1-10}$-alkoxy radicals, $R^3$, $R^4$ and $R^5$ are each independently selected from hydrogen, halogen, hydroxyl, $C_{1-10}$-alkyl, $C_{5-8}$-cycloalkyl, $C_{6-12}$-aryl, $C_{1-10}$-alkoxy, —$X^1$—C(O)OR$^6$, —C(O)R$^7$, —C(O)OR$^8$ or —C(O)NR$^9$R$^{10}$, or $R^3$ and $R^4$ together form a fused ring having from 5 to 7 ring members, $X^1$ is $C_{1-10}$-alkylene, $R^6$, $R^7$ and $R^8$ are independently selected from $C_{1-10}$-alkyl, $C_{6-12}$-aryl or $C_{7-11}$-aralkyl, and $R^9$ and $R^{10}$ are independently selected from hydrogen, $C_{1-10}$-alkyl, $C_{6-12}$-aryl or $C_{7-11}$-aralkyl.

2. The process of claim 1 wherein the Friedel-Crafts catalyst is selected from $BF_3$, $BCl_3$, $BBr_3$, $BeCl_2$, $ZnCl_2$, $GaCl_3$, $GaBr_3$, $BiCl_3$, $SbCl_3$, $TiCl_4$, $ZrCl_4$ and $SbCl_5$, $AlCl_3$, $AlBr_3$, $FeCl_3$, $SnCl_2$, $SnCl_4$.

3. The process of claim 1, wherein the Friedel-Crafts catalyst is used in an amount of 1.0 to 5 moles per mole of 2-chlorothiobenzoyl chloride (A).

4. The process of claim 1, wherein the Friedel-Crafts solvent is selected from methylene chloride, 1,2-dichloroethane, 1,1,2,2-tetrachloroethane, dichlorobenzene, carbon disulfide and nitrobenzene.

5. The process of claim 1, wherein the Friedel-Crafts solvent is the aromatic compound represented by Formula III.

6. The process of claim 1, wherein the Friedel-Crafts solvent is additionally present in the reactant mixture before the latter is added to the slurry.

7. The process of to claim 6, wherein the reactant mixture is dissolved in a Friedel-Crafts solvent, in an amount of 1 to 300 parts by weight per part by weight of the reactant mixture.

8. The process of claim 1, wherein the slurry contains 1 to 200 parts by weight of the Friedel-Crafts solvent per part by weight of the catalyst.

9. The process of claim 1, wherein the reactant mixture contains from 1 to 20 moles of the aromatic compound represented by Formula III per mole of the 2-chlorothiobenzoyl chloride.

10. The process of claim 1, wherein the reaction mixture is added to the slurry at a temperature in the range of −10 to 50° C.

11. The process of claim 10, wherein, following the addition of the reactants to the slurry, the resultant mixture is stirred at a temperature in the range of 0 to 80° C. for a period of from 20 minutes to 2 hours.

12. The process of claim 1, wherein the 2-chlorothiobenzoyl chloride has previously been purified by vacuum distillation at a temperature of from 80° C. to 200° and a pressure of from 0.1 to 300 mm Hg.

13. The process of claim 1, wherein the 2-chlorothiobenzoyl chloride has previously been purified by vacuum distillation at a temperature of from 80° C. to 200° C. and a pressure of about 10 mm Hg.

* * * * *